United States Patent [19]

Hesse

[11] Patent Number: 4,554,105

[45] Date of Patent: Nov. 19, 1985

[54] PROCESS FOR THE PREPARATION OF 1-HYDROXYLATED VITAMIN D COMPOUNDS

[75] Inventor: Robert H. Hesse, Cambridge, Mass.

[73] Assignee: Research Institute For Medicine and Chemistry Inc., Cambridge, Mass.

[21] Appl. No.: 648,309

[22] Filed: Sep. 7, 1984

Related U.S. Application Data

[63] Continuation of Ser. No. 568,620, Jan. 6, 1984, abandoned, which is a continuation of Ser. No. 438,604, Nov. 2, 1982, abandoned.

[30] Foreign Application Priority Data

Nov. 2, 1981 [GB] United Kingdom ................. 8133019
Nov. 2, 1981 [GB] United Kingdom ................. 8133021

[51] Int. Cl.$^4$ .............................................. C07J 9/00
[52] U.S. Cl. .................................................. 260/397.2
[58] Field of Search ...................................... 260/397.2

[56] References Cited

U.S. PATENT DOCUMENTS 4,202,829  5/1980  De Luca et al. ................. 260/397.2
4,297,289 10/1981  De Luca et al. ................. 260/397.2
4,338,250  7/1982  De Luca et al. ................. 260/397.2

FOREIGN PATENT DOCUMENTS 2058793  4/1981  United Kingdom ............. 260/397.2

OTHER PUBLICATIONS

Synthesis of Calcitroic Acid, Metabolite of 1 25-Dihydroxychlocecalciferol, Robert P. Esvelt, et al., *Journal Organic Chemistry*, 1981, vol. 46, pp. 456-458.

A Stereocontrolled Partial Synthesis of 1 -Hydroxy Vitamin $D_3$, Luc J. Vanmaele, et al., *Tetrahedron Letters*, vol. 23, No. 9, pp. 995-998, 1982.

Selenium Dioxide Oxidation of Cholecalciferol, Bohumil Pelc, Steroids, vol. 30, No. 2, Aug. 1977, pp. 193-201.

Direct C-1 Hydroxylation of Vitamin D compounds: Convenient Preparation of 1-Hydroxyvitamin $D_3$, 1 25-Dihydroxyvitamin $D_3$, and 1-Hydroxyvitamin $D_2$, Herbert F. Deluca, *Proceedings National Academy of Science, U.S.A.*, vol. 75, No. 5, pp. 2080-2081, May 1978.

Direct C (1) Hydroxylation of Vitamin $D_3$ and Related Compounds, Herbert E. Paaren, et al., *Journal Organic Chemistry*, 1980, 45, pp. 3253-3258.

*Primary Examiner*—Elbert L. Roberts
*Attorney, Agent, or Firm*—Bacon & Thomas

[57] ABSTRACT

1-unsubstituted 5,6-trans vitamin D compounds are 1α-hydroxylated by $Se^{IV}$ oxidation in the presence of selenous acid at a pH in the range 3-9. The oxidation is preferably effected using a 1-unsubstituted-3-trihydrocarbylsilyloxy-5,6-trans vitamin D compound in the presence of a co-oxidant.

10 Claims, No Drawings

PROCESS FOR THE PREPARATION OF 1-HYDROXYLATED VITAMIN D COMPOUNDS

This application is a continuation of application Ser. No. 568,620, filed Jan. 6, 1984; now abandoned which is a continuation of Ser. No. 438,604, filed Nov. 2, 1982, now abandoned.

The present invention relates to a process for the preparation of 1-hydroxylated Vitamin D compounds.

1α-Hydroxy vitamin D compounds, especially 1α-hydroxy vitamin $D_3$, are known to be useful in medicine for a variety of purposes and, for example, possess important prophylactic and therapeutic applications in the prevention or treatment of disorders such as rickets and osteomalacia and are of value in the treatment of both vitamin D responsive and vitamin D resistant diseases such as hypoparathyroidism, hypophosphataemia, hypocalcaemia and/or associated bone disease, renal disorders or renal failure and hypocalcaemic tetany. Furthermore, the activity of these compounds and their rapid onset and termination of activity render them of value in cases where vitamin D should be avoided because of its cumulative toxicity, in particular in the treatment of disorders such as vitamin D resistant rickets, renal osteodystrophy, steatorrhea, biliary cirrhosis and other malfunctions of absorption, osteoporosis, secondary hypocalcaemia and/or bone disease arising from dysfunction of the liver, kidneys or gastrointestinal tract, and secondary hypocalcaemia, osteoporosis or other bone diseases resulting from treatment with steroids, such as corticoids, diphenylhydantoin, barbiturates such as phenylbarbitone, and related drugs, which prove refractory to conventional compounds such as vitamin $D_3$.

Processes for the preparation of 1α-hydroxyvitamin $D_3$, and the analogues thereof have been described in the literature, but the yield obtained is low and in certain cases a mixture of products is obtained from which it is very difficult to separate the desired product. Most published processes involve the preparation of a suitably substituted steroidal 5,7-diene followed by the known photochemical and thermal isomerization to the desired 1-hydroxy vitamin D analogue. These processes are multi-stage, complex and give small yields thus rendering them uneconomic for commercial production. The direct allylic hydroxylation of vitamin $D_3$ with selenium dioxide is described by Pelc B; (1977) Steroids 30, 193–201, but the yield of hydroxylated products does not exceed 5% and it is very difficult to separate the various products of the mixture. Similar results were obtained by Deluca H. F. et al. Proc. Natl. Acad. Sci. U.S.A. Vol. 75 No. 5 pp. 2080–2081 (May 1978) and the preparation of 1α-hydroxy vitamin D from 3,5-cyclovitamin D described therein also involves a multi-stage low yield process.

Although, in view of the very high activity of 1α-hydroxy vitamin $D_3$, and the analogues thereof, processes having relatively low yields, e.g. of the order of 15%, may be sufficiently economic for commercial production, known processes are not capable of achieving even these low yields, and are not therefore well adapted for commercial production.

There is therefore a need for a process which will enable 1-hydroxyvitamin D compounds to be prepared more simply and/or in higher yields than hitherto possible, thus providing a process which would be sufficiently economic for commercial production.

Our South African Patent No. 79/5958 describes a novel process for the 1α-hydroxylation of a 1-unsubstituted 5,6-trans vitamin D compound in which the latter is reacted with a selenite ester, which may be generated in situ by reaction of selenium dioxide or selenous acid and an alcohol. The 5,6-transvitamin product may then be isomerised to the active 5,6-cis isomer by known techniques in high yield. The overall process provides the desired 1α-hydroxy vitamin D compounds in far higher yields than previously proposed direct 1α-hydroxylation procedures.

We have now found that direct 1α-hydroxylation of 5,6-trans vitamin D compounds can also be achieved in high yield even without the use of an alcohol, if selenous acid is present in the reaction mixture at a pH in the range 3–9.

Thus according to one feature of the present invention there is provided a process for the 1α-hydroxylation of vitamin D compounds by $Se^{IV}$ oxidation which comprises the oxidation of a 1-unsubstituted 5,6-trans vitamin D compound in the presence of selenous acid at a pH in the range 3–9.

It will be appreciated that in substantially non-aqueous media, ionisation of acids may not take place to give a measurable pH value consequently reference to the pH range 3–9 includes equivalent levels of acidity in substantially non-aqueous media. In such cases, in order to determine the acidity, the medium can be contacted with water and the pH of the aqueous phase determined.

The term "vitamin D compounds" as used herein includes nor-vitamin D compounds having shorter 17β-side chains than vitamin D.

In one embodiment, the selenous acid can be generated in situ by using selenium dioxide as reagent in the presence of a limited quantity of water. It will be appreciated that the water reacts with the selenium dioxide to produce selenous acid at a relatively slow rate which is in part dependent on the water concentration or the ratio of water to selenium dioxide. If the rate of production of the selenous acid is approximately the same as or less than its rate of reduction, the pH will not fall significantly even though selenous acid is a strong acid (pK < 1) and no pH control or buffer system may be necessary. Nevertheless, it is preferred to effect the reaction in the presence of an amine which in many cases will be provided by the use of N-methyl morpholine N-oxide as re-oxidant. The water may, in fact be added, at least in part, in the form of partially hydrated selenium dioxide or hydrated reactants such as N-methyl morpholine N-oxide monohydrate referred to below.

When using selenium dioxide itself as oxidant, together with water, the ratio of $SeO_2:H_2O$ should preferably be in the range 0.1 to 50; since the reaction rate tends to diminish with water concentration this ratio is advantageously 1.0 to 15.

The solvent for the reaction is not critical but preferably dissolves all the reactants. Suitable solvents include nitriles, e.g. $C_{1-6}$ aliphatic nitriles such as acetonitrile, halogenated hydrocarbons such as chloroform, dichloromethane or dichloroethane, hydrocarbon solvents such as hexane, ether solvents such as diethyl ether, amides such as dimethyl formamide, nitroalkanes such as nitromethane and alcohols such as methanol or ethanol.

Where selenous acid is used as oxidant directly, rather than being formed from selenium dioxide and water, the reaction mixture is preferably buffered. In general the pH is preferably in the range 3-6. Suitable buffers include tertiary amines in admixture with their salts, for example trialkylamines or N-methyl saturated heterocyclic amines such as N-methyl morpholine in admixture with salts such as hydrochloride or tosylate salts. In general an amine salt as such, providing relatively acidic conditions, tends to speed the reaction.

Alternatively, a salt of a strong base with selenous acid can be used, which being a salt of a strong base with a strong acid, will normally have a pH about 7.0. In order to achieve good solubility in solvent systems which are essentially anhydrous, the base is preferably one giving salts with selenous acid which are soluble in such solvents. Tetraalkylammonium salts such as tetramethyl or tetraethylammonium salts are especially suitable. Since, however, selenous acid rather than selenite ion is the active oxidant, a hydrogen selenite salt is preferred.

If the reactants are selenous acid and an amine base, about 0.3 to 1.6 equivalents of base are preferably used, relative to the selenous acid. At higher levels of base, the reaction becomes rather slow due to the low concentration of free selenous acid.

The oxidation may also be effected by the use of a selenite ester as described in South African Patent No. 79/5958 in the presence of water and at a pH in the range 3-9. Preferred selenite esters in this regard include dimethyl selenite, diethyl selenite and ethylene selenite, for example 0.5 to 1 equivalents thereof. The water may, for example, be present in the form of hydrated reactants.

The 5,6-trans vitamin D compounds used as starting materials may, for example, be represented by the formula:

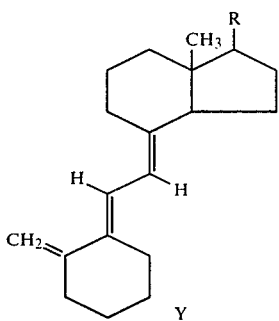

wherein Y represents a hydrogen atom or a hydroxyl or protected hydroxyl group and R represents a group of the formula:

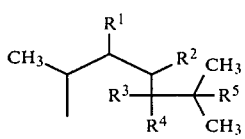

wherein $R^1$ and $R^2$, which may be the same or different, each represents a hydrogen or halogen atom or a hydroxy or protected hydroxy group or together from a carbon-carbon bond or an epoxy group, $R^3$ and $R^5$, which may be the same or different, each represents a hydrogen or halogen atom or a hydroxy or protected hydroxy group, and $R^4$ represents a hydrogen or halogen atom or a methyl or ethyl group, or $R^3$ and $R^4$ together represent a keto or protected keto group.

1-unsubstituted-5,6-trans nor vitamin D compounds may also be used as starting material and for example possess the formula:

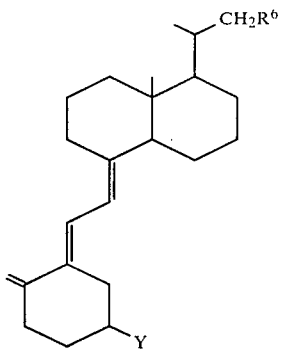

wherein Y is as hereinbefore defined and $R^6$ represents a hydroxy group or a reactive derivative thereof e.g. a hydrocarbylsulphonyloxy group e.g. a toluenesulphonyloxy group.

Where Y represents a protected hydroxyl group this may be an esterified or etherified hydroxyl group e.g. an alkanoyloxy group having 1 to 6 carbon atoms such as an acetoxy, propionyloxy, isobutyryloxy or pivaloxy group, an aroyloxy group having 7 to 15 carbon atoms e.g. a benzoyloxy or 4-phenylazobenzoyloxy group, a lower alkoxy group having 1 to 6 carbon atoms which may be interrupted by an oxygen atom such as a methoxy or methoxymethoxy group, a tetrahydropyranyloxy group or a trihydrocarbylsilyloxy group e.g. with 3 to 9 carbon atoms such as a trimethyl- or tri-ethyl silyloxy group or an n-butyldimethylsilyloxy group.

Although such protected forms are in general physiologically active, the free hydroxy forms are preferred for use in medicine. The protecting groups may be deprotected e.g. by conventional methods which methods are well documented in the literature. Thus, acyloxy groups of esters may be removed by basic hydrolysis e.g. with alkali metal alkoxide in an alkanol. Since the triene system of the vitamin D compound is sensitive to acids, acid hydrolysis to remove trihydrocarbylsilyloxy groups must be effected carefully; under mild conditions, a preferred method is treatment with tetra-alkyl ammonium fluorides.

A 5,6-trans starting compound of formula I may, for example, be used in which the 17-side chain R represents the group

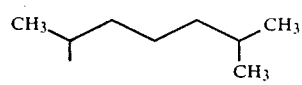

as in vitamin $D_3$.

Thus, for example the starting compound may have the 17-side chain of a 5,6-trans vitamin $D_3$ or a 5,6-trans vitamin $D_2$.

The 5,6-trans vitamin D compound will, in general, be formed by isomerisation of the corresponding natural 5,6-cis compound, for example using conventional methods such as treatment with iodine, a Lewis acid such as $BF_3$ or diphenyldiselenide. We have recently found, however, that isomerisation can be effected in high yield by conversion of the cis vitamin to an SO$_2$ adduct followed by heating in the presence of a base to remove the SO$_2$ whereby the trans vitamin is the predominant product.

The preparation of 1-unsubstituted-5,6-trans nor vitamin D compounds is described in our copending British and European Patent Applicatigns filed 2 Nov. 1982 under the title "Chemical Compounds". Thus for example the nor-vitamin D compounds used as starting materials in tne present invention may be prepared by stabilization of vitamin D$_2$ by formation of a Diels Alder dienophile adduct e.g. by reaction with sulfur dioxide, oxidative cleavage of the 17$\beta$-side chain e.g. by ozonolysis to form an aldehyde and reduction of the aldehyde to form an alcohol and subsequent reaction to form a reactive derivative thereof such as a tosylate, the dienophile residue being removed for example by thermolysis e.g. under basic conditions.

The oxidation of 5,6 trans vitamin D compounds according to the invention may take place in the presence of the corresponding 5,6-cis isomers, for example a mixture resulting from incomplete isomerisation of the 5,6-cis starting compound. Although direct oxidation of 5,6-cis isomers with selenium dioxide tends to yield large quantities of unwanted by-products, as is seen from the poor results reported in the prior art (where no alcohol was present), this reaction is far slower than the allylic oxidation of the trans-isomer the cis-isomer is thus largely either left unoxidised, or is isomerised.

Although in these cases the 5,6-trans starting material has to be prepared by isomerisation in a separate step prior to oxidation, we have found that the 5,6-cis vitamin D compounds of formula (I) are oxidised very slowly indeed by selenium dioxide. It is thus possible to prepare a mixture, e.g. an equilibrium mixture, of the 5,6-cis and 5,6-trans isomers and to continue the oxidatioh with selenium dioxide until a substantial amount e.g. at least 60%, preferably about 80%, of the 5,6-trans isomer has been oxidised. In this connection the course of the reaction may be monitored by, for examp.le, thin layer chromatography. The unreacted 5,6-cis vitamin D analogue may then, if desired, be subjected to another isomerisation step and used in the oxidation reaction again. In these circumstances it is unnecessary to separate mixtures of cis and trans isomers prior to the oxidation. It is especially advantageous that there is no need to separate cis and trans isomers prior to the oxidation reaction, since isomerisation of the cis to the trans isomers commonly results in an equilibrium mixture in which the ratio of trans to cis isomers is about 3:2.

The oxidation reaction is, in general, conveniently effected at a temperature of from ambient temperature (e.g. about 10°-25° C.) up to the boiling temperature of the reaction mixture, e.g. an elevated temperature, preferably, at about the boiling temperature of the reaction mixture.

The process of the present invention as described above has been found to result in yields of about 15-20% which yields are sufficiently high to render such processes economic for commercial production having regard to the high activity of 1$\alpha$-hydroxyvitamin D compound.

In this connection we have found that if the starting vitamin D compounds do not have a bulky group present in the 3-position e.g. have a free 3-hydroxyl group or a 3-hydroxyl group protected by a lower (i.e. C$_{1-6}$) ester or ether such as an acetate or methyl ether, the initial 5,6-cis vitamin D compounds are isomerised in situ in the oxidation reaction and thus it may not be necessary to effect the isomerisation in a separate step prior to the oxidation.

We have also found, however, that where a bulky group, for example a bulky ester group such as a pivalyloxy, isobutyryloxy, benzoyloxy or 4-phenylazobenzoyloxy group, is present in the 3-position; 5,6-cis vitamin D compounds do not isomerise satisfactorily under the conditions of the oxidation.

In a further preferred embodiment of the present invention we have been able to increase still further the yield of 1-hydroxyvitamin D compounds by the use of a co-oxidant capable of oxidising Se$^{II}$ compounds to Se$^{IV}$ compounds. Indeed we have achieved yields as high as 60% by the use of such co-oxidants. Co-oxidants include for example, the metal salts of per acids, for example the metal salts of periodic acid, preferably the alkali metal salts of periodic acid, especially sodium metaperiodate. Certain alkyl hydroperoxides and tertiary amine oxides have been found to be especially advantageous for use as co-oxidants in view of the relatively clean oxidation reaction which can be effected under mild conditions.

The hydroperoxides of particular interest as co-oxidants are tertiary alkyl hydroperoxides in which the alkyl moiety may, if desired, be substituted by one or more aryl groups. Thus, for example, the hydroperoxide may have the formula

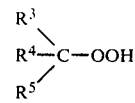

which may be the same or different, each represent alkyl e.g. methyl or aralkyl e.g. benzyl groups, the hydro-peroxide advantageously having from 4 to 16 carbon atoms e.g. t-butyl hydroperoxide.

The tertiary amine oxides of particular interest as co-oxidants are non-aromatic tertiary amine oxides, for example compounds of the formula:

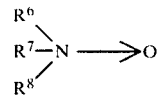

wherein R$^6$, R$^7$ and R$^8$, which may be the same or different, each represents an alkyl or aralkyl group or any two of R$^6$, R$^7$ and R$^8$ may represent, together with the nitrogen atom to which they are attached, a saturated heterocyclic group which may contain one or more further hetero atoms, for example one or more nitrogen, oxygen or sulfur atoms, the amine oxide advantageously having 3-15 carbon atoms. Thus for example the tertiary amine oxide may be a trialkylamine or a heterocyclic compound such as N-methyl morpholine N-oxide. It should be noted that the tertiary amine liberated in the oxidation reaction exerts a beneficial buffering effect.

1 to 10 preferably about 2-4 molecular equivalents of the co-oxidant are conveniently used per molecular equivalent of the 5,6-trans starting material used.

The selenium dioxide is conveniently used in an amount ranging from 0.3 to 1.5, preferably about 1.0 molecular equivalents per molecular equivalent of 5,6- trans starting material. Where no co-oxidant is used the ratio of selenium dioxide to 5,6-trans starting material is preferably about 1:1. Selenous acid is conveniently used in the same proportions.

The oxidation reaction normally will yield predominantly 1α-hydroxy-5,6-trans vitamin D compounds but minor quantities of its β-isomer may be formed and where a small group is present at the 3-position, also minor quantities of 1α- and 1β-hydroxyvitamin $D_3$ cisisomer. Yields of 1α-hydroxy-5,6-transvitamin $D_3$ of the order of 44% have been obtained using 5,6-trans-vitamin D derivatives having a relatively bulky ester grouping at the 3-position and using sodium metaperiodate as co-oxidant a further 18% of 1β-hydroxy-5,6-transvitamin D being formed simultaneously. Where the 3-position carries a trihydrocarbylsilyloxy group, we have found that the ratio of 1α- to 1β-isomer is dramatically increased to for example, about 20:1. Such protecting groups are, therefore, preferred.

Thus according to a particularly preferred embodiment of the present invention there is provided a process for the 1α-hydroxylation of vitamin D compounds by $SE^{IV}$ oxidation which comprises the oxidation of a 1-unsubstituted-3-trihydrocarbylsilyloxy-5,6-trans-vitamin D compound at a pH in the range 3–9 in the presence of selenous acid and a co-oxidant capable of oxidising $Se^{II}$ compounds to $Se^{IV}$ compounds.

The 3-trihydrocarbylsilyloxy derivatives of the starting vitamin D compound (which carries a 3β-hydroxy group) may be prepared by reacting the latter with a suitable reagent such as a trihydrocarbylsilyl-amide or halide. Where a halide is used, an acid binding agent is preferably present, for example an organic base such as triethylamine, dimethylaminopyridine, or more preferably imidazole. This protection step may be carried out before or after isomerisation of the 5,6-cis to the 5,6-trans vitamin D compound.

1-Hydroxytransvitamin D compounds may, if desired, be converted into the corresponding cis compound by isomerization methods well known from the literature e.g. by treatment with iodine, a Lewis acid or diphenyldiselenide or more preferably by photo isomerisation in the presence of a triplet sensitizer having a triplet energy of about $45 \pm 5$ Kcal per mole, for example anthracene, acridine or phenazine.

The 1α-hydroxy compounds are of particular interest in that 1α-hydroxyvitamin $D_3$ (cis-isomer) and many of its analogues are of great value in medicine while the 1α-hydroxy-5,6-transvitamin D compounds may either be converted into their 5,6-cis isomers as described herein or used as an intermediate in the production of 1α-hydroxydihydrotachysterols by conventional methods well known in the literature.

The 1β-hydroxy-material may be separated from the 1α-hydroxymaterial by conventional methods such as chromatography or even by direct crystallisation. The undesired 1β-isomer may if desired subsequently be converted into the 1α-isomer according to known isomerisation techniques e.g. directly or, more preferably, by oxidation with an allylic oxidant, e.g. manganese dioxide, to the corresponding 1-oxo steroid followed by stereospecific reduction with a metal hydride e.g. lithium aluminium hydride or sodium borohydride.

The isomerisation of 1β-hydroxy-5,6-trans vitamin D compounds to the desired 1α-hydroxy-5,6-cis vitamin D compounds thus requires two isomerisation steps; the isomerisation at the 1-position is preferably effected first.

In the case where a 3-trihydrocarbylsilyloxy substituent is present, by reducing the proportion of 1β-hydroxy isomer to only about 5%, subsequent isomerisation of this to the 1α-isomer, as described in our above South African Patent Specification is rendered unnecessary. Indeed, since the 1β-hydroxy isomers are physiologically harmless there may be no need to remove the small amount which is formed and in some cases the 1α-hydroxy vitamin D compound may be used without such removal.

Furthermore, isolation of the desired 1α-isomer is much easier when a 3-silyloxy group is present.

The present invention thus also relates to the isomerisation of a 1-hydroxy-5,6-trans vitamin D compound obtained according to the above-described process to the 1α-hydroxy-5,6-vitamin D compound (i.e. the 5,6-cis isomers).

The products of the process of the present invention, e.g. 1α-hydroxyvitamin D compounds (i.e. 5,6-cis isomers) especially 1α-hydroxyvitamin $D_3$, may be formulated into pharmaceutical compositions in the conventional manner.

Thus according to a further feature of the present invention there are provided pharmaceutical compositions comprising a 1α-hydroxy vitamin D compound, especially 1α-hydroxyvitamin $D_3$, prepared according to the process hereinbefore described as active ingredient in association with a pharmaceutical carrier or excipient.

The following Preparations and Examples are given by way of illustration only:

All reactions were done in the dark and under argon. They are monitored by TLC on pre-coated TLC sheets SILICA GEL 60 F - 254 (Merck) with hexane-ethyl acetate 3:1 as eluant. Preparative TLC was carried out with SILICA GEL GF 1000 microns precoated plates (ANALTECH): The eluant mixture is generally: hexane-ethyl acetate 4:1 NMR resonances are given in ppm from TMS as internal reference.

Aqueous work-up refers to partition between an organic solvent and water, followed by sequential washing with a 5% aqueous sodium bicarbonate solution and a saturated aqueous soidium chloride solution. The organic solution was dried using either anhydrous $MgSO_4$ or anhydrous $Na_2SO_4$, and the solvent removed on a rotary evaporator. Acid work-up refers to partition between an organic solvent and water, followed by sequential washing with a 4% aqueous HCl solution; 5% aqueous sodium bicarbonate solution, etc. as for aqueous work-up.

PREPARATION 1

Isomerisation of cis vitamin $D_3$

A benzene solution of cis vitamin $D_3$ (1g. in 20 ml) is vigorously stirred for 3 hrs. in the presence of a saturated aqueous $SO_2$ solution (10 ml). After dilution with ether, the organic phase is neutralised with saturated sodium bicarbonate aqueous solution, washed with water and dried over $Na_2SO_4$ and evaporated in vacuo to afford 1.08g of crude cyclic sulfones. $^1$H-NMR $(CDCl_3):\delta 0.54$ (s, 1.2H, $C_{18}$-H)0.64 (s, 1.8H, $C_{18}$-H)3.6 (m, 2H, C.19-H) 4.0 (m, 1H, $C_3$-H) 4.55 to 4.85 (m, 2H, C.6-H and C.7-H).

The crude $SO_2$ adducts (1.08g) are dissolved in methanol or absolute ethanol (25 ml), in the presence of sodium bicarbonate (1 g). The heterogeneous mixture is refluxed for 2 hrs. After filtration of the coded reaction mixture, the alcohol is distilled in vacuo. The residue is dissolved in ether, washed with water, dried over Na$_2$SO$_4$ and the ether is distilled in vacuo to afford 0.91g of transvitamin D$_3$ as a foam. $^1$H-NMR (CDCl$_3$):δ0.54 (s, 3H, C$_{18}$-H) 3.7 (m. W1/2 =17Hz, C$_3$-H) 4.6 and 4.9 (2m, 2H, C-19.H) 5.88 and 6.52 (AB system, J$_{AB}$=11.5 Hz, 2H, C-6-H and C-7-H).

PREPARATION 2

Silylation (a) Trimethylsilylation:

A benzene solution of transvitamin D$_3$ (1 g in 5 ml) is stirred overnight at room temperature, in the presence of bis-trimethylsilylacetamide (1 ml). After concentration in vacuo, the residue is chromatographed on silica with hexane to afford 785 mg of the 3-treimethsilyl ether (66% non-optimized yield) $^1$H NMR (CCl$_4$)δ0.08 (s, 9H, Me$_3$ Si) 0.53 (s, 3H, C$_{18}$-H) 0.7 to 1 (m, 9H, CH$_3$ 21–26 and 27) 3.4 to 4.0 (m, W1/2=19 Hz, 1H, C$_3$-H) 4.53 and 4.8 (2m, 2H, C$_{18}$-H). 5.7 and 6.3 (AB system J$_{AB}$=11Hz, 2H, C$_6$ and C$_7$ - H).

(b) t-butyldimethylsilylation:

(i) DMAP - method:

To a cooled (5° C.) solution of transvitamin D$_3$ (295 mg), p-dimethylaminopyridine (65 mg. 0.7 eq) triethylamine (171 mg, 2 eq.) in DMF (5 ml) is added a solution of t-butyldimethylsilylchloride (230 mg, 2 eq.) in DMF (3 ml). After 48 hours at room temperature, the mixture is diluted with ether and washed with water. After drying over Na$_2$SO$_4$, the organic phase is concentrated in vacuo and the residue is chromatographed on Prepplate to afford 265 mg. of 3-t-butyldimethylsilyloxy transvitamin D$_3$ as a foam (63%).

(ii) Imidazole method:

To a cooled (5° C.) solution of transvitamin D$_3$, (1.64 g) and imidazole (582 mg., 2eq) in DMF (7 ml) is added dropwise a solution of t-butyldimethylsilyl chloride (993 mg., 1.5eq) in DMF (3.5 ml). After 3 hrs at room temperature, the reaction mixture is worked up, and chromatography on silica gel (24 g) with hexane yields 2.06g of 3-t-butyldimethylsilyloxy transvitamin D$_3$ (97%) as an oil. $^1$H NMR (CDCl$_3$):δ0.08 (s, 6H, Me$_2$ Si) 0.57 (s, 3H, C$_{18}$-H). 0.8 to 2.05 (m, 18H, C$_{21}$-H, C$_{26}$-H, C$_{27}$-H and Me$_3$ C-Si) 3.9 (m, W1/2=17 Hz, 1H, C$_3$-H) -4.7 and 4.96 (2m, 2H, C$_{19}$-H) 6.0 and 6.63 (AB system, J$_{AB}$=11.5 Hz, 2H, C$_6$-H and C$_7$-H).

(CCl$_4$):δ0.63 (s, 3H, C$_{18}$-H) 3.90 (m, W1/2=17 Hz, 1H, C$_3$-H) 4.63 and 4.9 (2m, 2H, C$_{19}$-H). 5.83 and 6.56 (AB system, J$_{AB}$=11.5 Hz, 2H, C$_6$-H and C$_7$-H).

3-t-butyldimethylsilyloxy cis vitamin D$_3$ from cis vitamin D$_3$: yield - 95% - oil. 1H NMR (CCl$_4$):δ0.08 (s, 6H, Me$_2$ Si) 0.60 (s, 3H, C$_{18}$H) 0.7 to 1.1 (m, 18H, C$_{21}$-H, C$_{26}$-H, C$_{27}$-H and Me$_3$ C-Si). 3.5 to 4.06 (m, W1/2=17 Hz 1H, C$_3$-H) 4.7 and 4.93 (2m, 2H, C$_{19}$-H) 5.87 and 6.07 (AB system, J$_{AB}$=11 Hz, C$_6$ and C$_7$-H).

PREPARATION 3

Silylation of 25-hydroxy transvitamin D$_3$ 25-hydroxy transvitamin D$_3$ (also known as (E) 3,25-calcifediol) (190 mg.) in DMF (2 ml.) is treated with triethylchlorosilane (0.25 ml., 0.224g, 3 eq.) in the presence of imidazole (136 mg. 4 eq.). The mixture is stirred for 2 hrs. 30 at R.T. After work-up, prep TLC (hexane-ethyl acetate 20-1) yields 219 mg. of 3,25-bis triethylsilyloxy transvitamin D$_3$ (also known as 3,25-bis triethylsilyloxy (E) - calcifediol) as an oil (73%). $^1$H HMR (CDCl$_3$):δ0.4 to 1 (m, 24 H, (Me - CH$_2$)$_3$ Si, CH$_3$ -18, CH$_3$ - 21) 1.2 (s, 6H, CH$_3$ - 26 and 27) 3.47 and 4.1 (m, W1/2=19 Hz, 1H, C$_3$ - H) and 4.63 and 4.93 (2m, 2H, C-19 H). 5.86 and 6.53 (AB system, J$_{AB}$=11 Hz, C$_6$-H and C$_7$-H).

PREPARATION 4

9,10-seco-3β-(triethylsilyloxy)-20(S)-(p-toluenesulphonyloxymethyl)-pregna-5(E),7(E),10(19)-triene (i) SO$_2$ adducts of 9,10-seco-3β-hydroxy-ergosta-5(Z),7(E), 10(19),22(E)-tetraene Sulphur dioxide was slowly passed through a well-stirred mixture of benzene (100 ml) and water (50 ml) containing ergocalciferol (5g), for a total of 3.5 hr. After this time, air was passed through the mixture for approx 20 min. Ether and brine were added and the layers separated. Aqueous work-up gave the known sulphur dioxide adducts which were used without further purification.

(ii) SO$_2$ adducts of 9,10-seco-3β-triethylsilyloxy-ergosta-5(E),7(E),10(19),22(E)-tetra-ene The crude mixture of sulphur dioxide adducts of ergocalciferol (prepared from 5g of ergocalciferol as described previously), in CH$_2$Cl$_2$ (40 ml), containing imidazole (4g) was stirred with triethylsilylchloride (3.5 ml). After about 30 min, water was added and the organic later washed with water/brine and dried. The required silyl ether was isolated to give, after chromatography, 5.3g (74% from ergocalciferol) as an oil. $^1$Hnmr δ 5.22 (m, W=9Hz, C-22H, 23H), 4.64 (m, W=10Hz, C-6H, 7H) 4.02 (m, W=16Hz, C-3H), 3.67 (broad s, C-19H$_2$).

(iii) SO$_2$ adducts of 9,10-seco-3β-(trimethylsilyloxy)-20(S)-formyl-pregna-5(E),7(E),10(19)-triene The SO$_2$ adducts from (ii) above (5g) in CH$_2$Cl$_2$ (180 ml) and methanol (60 ml) were cooled to −78° C. The efficiently mixed solution was treated with an ozone-oxygen mixture (approx. 1 mmol O$_3$/min) for 8–12 min (tlc control) and then thoroughly purged with dry argon for approx. 5 mins. Triphenyl phosphine (3g) was added and the mixture, after approx. 30 mins at −78° C. (tlc monitoring of the methoxy-hydroperoxide intermediates) was shaken with 5% aqueous NaHCO$_3$ (to prevent dimethyl acetal formation) and allowed to warm to room temperature. The layers were separated and the organic solution dried. Chromatography through silica gel (50g) gave the aldehyde of the title in 82% yield free from any of C-20(R)epimer.

$^1$Hnmr δ9.57 (m, C-22H), 4 67 (m, W=12Hz, C-6H, 7H), 3.97 (m, W=16Hz. C-3H), 3.65 (broad s, C-19H$_2$), 1.15 (d, J=6Hz, C-21H$_3$); IR νmax (thin film) 2950 (s), 2900 (sh), 1735 (s), 1660 (w), 1460 (m), 1380 (m), 1310 (s), 1150 (m), cm$^{-1}$.

(iv) SO$_2$ adducts of 9,10-seco-3β-(triethylsilyloxy)-20-(S)-(hydroxymethyl)-preqna-5(E),7(E),10(19)-triene The SO$_2$ adducts from (iii) above (3g) in benzene (75 ml) were added dropwise over a 15–20 min. period to sodium borohydride (0.9g) in ethanol (25 ml). After the addition, the excess reducing agent was carefully quenched with dilute aqueous HCl. The mixture was diluted with CH$_2$Cl$_2$. Aqueous work-up gave the title alcohol in greater than 90% yield.

$^1$Hnmr δ4.63 (m, W=12Hz. C-6H. 7H), 3.93 (m, W=16Hz, C-3H), 3.77–3.17 (m, C-19H$_2$, 22H$_2$); IR νmax (thin film) 3550 (br), 2950 (s), 2900 (sh), 1660 (w), 1460(m), 1380 (m), 1305 (s), 1240(m), 1155(m), cm$^{-1}$.

(v) 9,10-seco-3β-(triethylsilyloxy)-20(S)-(p-toluenesulphonyloxymethyl)pregna-5(E), 7(E), 10(19)-triene The crude $SO_2$ adducts of 9,10-seco-3β-triethylsilyloxy-20-(S)-(hydroxymethyl)-pregna-5(E), 7(E), 10(19)-triene from (iv) above (3.2g) was stirred overnight in pyridine (40 ml) at 5° C. with p-toluenesulphonyl chloride (4g). The reaction was cooled to 0° C., water added and, after a few minutes, the mixture diluted with $Et_2O$. After an acid work-up, the crude oily product (281) was taken up in ethanol (100 ml) and refluxed in the presence of $NaHCO_3$ (49) for 1 hr. The mixture was concentrated and partioned between $CH_2Cl_2$/water/brine. The organic solution was dried and chromatographed to give 2.64g (70%) of the required vitamin (278c) nmr and IR :-

$^1$Hnmr δ7.73 (d, J=8 Hz, 2H, aryl), 7.28 (d, J=8Hz, 2H, aryl), 6.43 and 5.81 (ABq, J=11 Hz, C-6H, 7H), 4.92 (s, C-19H), 4.63 (s, C-19H), 4.2–3.57 (m, C-3H, 22H$_2$), 2.48 (s, aryl-CH$_3$); IR νmax (thin film) 2960 (s), 2900 (sh), 1600 (w), 1460 (m), 1360 (s), 1190 (s), 1175 (s), 1090 (s), cm$^{-1}$.

EXAMPLE 1

Allylic hydroxylation: General Procedure (a) With diethylselenite:

A solution of N-methylmorpholine N-oxide, monohydrate (2 to 5 eq.) in methylene chloride (10 ml for 1 g. of vitamin derivative) is dried over anhydrous $MgSO_4$ for 30 min. and then filtered through glass-wool into the solution of the vitamin derivative in dry methanol (10 ml. for 1 g.) and dry 1,2-dichloroethane (10 ml. for 1 g.). The solution is heated until reflux, and diethylselenite (about 1 eq) is added. The reflux is maintained until TLC indicates a conversion of circa 80%. The orange-red reaction mixture is cooled, diluted with methylene chloride, washed with $NaHCO_3$ aqueous saturated solution, with water, and dried over $Na_2SO_4$. After concentration in vacuo, the residue is chromatographed on prep-plate (hexane-ethyl acetate (4-1) and elution of the various zones with ethyl acetate yields the 1-hydroxy compounds.

(b) With selenium dioxide:

The N-methylmorpholine N-oxide, monohydrate (2 to 5 eq.) in methylene chloride solution, dried as above, is filtered in the 1,2-dichloroethane solution of the vitamin (10 ml. per g. of vitamin) and the solution is heated until reflux. A solution of selenium dioxide (1 eq.) in dry methanol (10 ml. per g. of vitamin) which has been stirred for 45 min. at room temperature, is added to the vitamin solution and the mixture is refluxed and worked up as above.

The most frequently used amount of N-methylmorpholine N-oxide, monohydrate is 4 to 4.5 eq. 1α-Hydroxy 3-trimethylsilyloxy transvitamin $D_3$:Yield: 47% $^1$H NMR (CCl$_4$):δ0.15(s, 9H, Me$_3$ Si) 0.6 (s, 3H, C$_{18}$ - H) 0.8 to 1.06 (m, 9H, CH$_3$ 21, 26 and 27) 3.83 to 4.53 (2m, 2H, C$_1$ and C$_3$ - H) 4.9 and 5.0 (2m, 2H, C$_{19}$ - H). 5.83 and 6.43 (AB system, J$_{AB}$=11 Hz, C$_6$ and C$_7$ - H). 1β-hydroxy-3-trimethylsilyloxy transvitamin $D_3$: Yield: 2%. 1α-hydroxy 3-t-butyldimethylsilyloxy transvitamin $D_3$: Yield 52% $^1$H NMR (CCl$_4$):δ0.07 (s, 6H Me$_2$Si) 0.53 (s, 3H, C$_{18}$-H) 0.77 to 1 (m, 18H, CH$_3$ 21, 26 and 27 and Me$_3$ C-Si) 3.73 to 4.47 (2m, 2H C$_1$ and C$_2$ - H) 4.8 and 4.87 (2m, 2H, C$_{19}$ - H), 5.7 and 6.3 (AB system, J$_{AB}$=11 Hz, C$_6$ and C$_7$ - H). (CDCl$_3$):δ0.08 (s, 6H, Me$_2$Si) 0.55 (s, 3H, C$_{18}$ - H) 0.8 to 1.04 (m, 18H, CH$_3$ 21, 26, 27, Me$_3$ C-Si) 3.9 to 4.6 (2m, 2H, C$_1$ and C$_3$ - H) 4.9 and 5.05 (2m, 2H, C$_{19}$ - H) 5.84 and 6.51 (AB system, J$_{AB}$=11.5 Hz, 2H, C$_6$ and C$_7$ - H). 1β-Hydroxy-3-t-butyldimethylsilyloxy transvitamin $D_3$: Yield: 2%.

EXAMPLE 2

(E) to (Z) photoisomerisation

General procedure; The benzene or hexane solution of 1α-hydroxy-3-silyloxy transvitamin $D_3$ (3 to 14 mg/ml) and sensitizer (1 mg. for 10 mg. of vitamin) is deoxygenated by four cycles of vacuum (15 mm Hg) and argon, followed by flushing of argon for 30 min., in the dark, with internal cooling. The flask is then irradiated, with TLC monitoring:

either with a dark lamp (UVL - 22, λ=366 nm), placed in contact with the external side of the flask.

or with the Hanovia 654 A36 UV lamp (λ max 360 nm) immersed in a cooling pyrex jacket: The reaction flask is placed at a distance between 10 and 15 cm from the lamp.

The whole apparatus (lamp and reaction flask) is wrapped in aluminium foil. After concentration in vacuo, the residue is prep-chromatographed (hexane-ethyl acetate 4-1) to afford the 1α-hydroxy-3-silyloxy cisvitamin $D_3$ as slightly less polar than the transvitamin $D_3$ compound.

Yield: 3-trimethylsilyloxy: 78%—oil; 3-t-butyldimethylsilyloxy: 80%—foam. $^1$H nmr of 1α-hydroxy-3-trimethylsilyloxy cis vitamin $D_3$: (CCl$_4$):δ0.13 (s, 9H, Me$_3$ Si) 0.57 (s, 3H, C$_{18}$ - H) - 0.77 to 1.04 (9H, m, CH$_3$ 21, 26, 27) 3.83 to 4.5 (2m, 2H, C-1 and C$_3$ -H). 4.87 and 5.13 (2m, 2H, C$_{18}$ - H). 5.86 and 6.23 (AB system, J$_{AB}$=11 Hz, 2H, C$_6$ and C$_7$ - H).

EXAMPLE 3

1α-hydroxy cis vitamin $D_3$

1α-hydroxy 3-t-butyldimethylsilyloxy cis vitamin $D_3$ in dry THF (75 mg. in 1 ml) was treated with tetra n-butyl ammonium fluoride (4 ml. of 0.36 M solution in THF), 24 hrs. at room temperature, and 15 min. at reflux. The reaction mixture was diluted with benzene, washed with water, dried over $Na_2SO_4$ and concentrated in vacuo. After prep TLC (benzene-ethyl acetate 8 - 5) and elution with ethyl acetate, 51 mg. of 1α-hydroxy-cis vitamin $D_3$ are obtained as an oil (87%), and crystallizes from the ether - hexane (1-9) solution to yield 26 mg. of 1α-hydroxy-cis vitamin $D_3$. The remaining oil, suspended in hexane, and seeded, affords a second crop: 15 mg. m.p.: 135°–137° C. litt (10): 132–133 (11): 138°–139.5° C. $^1$H NMR CDCl$_3$):δ0.53 (s, 3H, C$_{18}$ - H) 0.08–0.90 (m, 9H, CH$_3$ 21, 26, 27) 3.90 to 4.60 (2m, 2H, C$_1$ - H and C$_3$ - H) 4.95 and 5.35 (2m, 2H, C$_{19}$ - H) 5.97 and 6.40 (AB system J$_{AB}$=11 Hz, C$_6$ - H and C$_7$ - H).

EXAMPLE 4

Oxidation of 3,25-bis triethylsilyloxy transvitamin $D_3$ 3,25-Bis triethylsilyloxy transvitamin $D_3$ (also known as 3,25 bis triethylsiloxy (E) calcifediol) (219 mg) prepared as described in Preparation 3 is treated by selenium dioxide (38.5 mg., 1 eq.) and N-methylmorpholine N-oxide monohydrate (265 mg. 5.5 eq.) in a mixture of methylene chloride (2 ml) 1,2-dichloroethane (2 ml) and methanol (2 ml) at reflux for 35 min. After work-up and prep - TLC (hexane - ethyl acetate 4-1). 1α-hydroxy-3,25-bis triethylsilyloxy transvitamin $D_3$ (also known as 1α-hydroxy-3,25-bis triethylsilyloxy (E) calcifediol) is obtained (123 mg, 55%), along with a less polar product (5 mg, 2%, possibly the 1β- epimer), and 15 mg. of recovered starting material (7%). $^1$H NMR of 1α-hydroxy: (CDCl$_3$ - CCl$_4$):δ0.4 to 1 (m, 24H, (Me-CH$_2$)3 Si, CH$_3$ - 18 and CH$_3$ - 21) 1.2 (s, 6H, CH$_3$ -26 and 27) 3.66 to 4.45 (2m, 2H, C$_1$ - H and C$_3$ - H) 4.8 and 4.9 (2m, 2H, C$_{19}$ - H) 5.73 and 6.37 (AB system, J$_{AB}$ - 11 Hz, 2H, C$_6$ - H and C$_7$ - H).

EXMPLE 5

(E) to (Z) Isomerisation

A dry benzene solution of 1α-hydroxy-3,25-bis triethylsilyloxy transvitamin D$_3$ (also known as 1α-hydroxy-bis triethylsilyloxy (E) - 3,25 calcifediol) (123 mg. in 25 ml) is irradiated, in the presence of phenazine (20 mg.) with a dark lamp UVL - 22 for 2 hr. Work-up and prep. - TLC (hexane - ethyl acetate 4-1) yield 103 mg. of 1α-hydroxy-3,25-bis triethylsilyloxy cis vitamin D$_3$ (also known as 3,25-bis triethylsilyloxy 1α,3β,25-calcitriol) (83%). $^1$H NMR (CCl$_4$):δ0.33 to 1.10 (m, 24H, ((Me)-CH$_2$)$_3$ Si, CH$_3$ - 18 and 21) 1.17 (s, 6H, CH$_3$ - 26 and 27) 3.79 to 4.47 (m, 2H, C$_1$ - H and C$_3$ - H) 4.87 and 5.17 (2m, 2H, C$_{19}$- H) 5.87 and 6.20 (AB system J$_{AB}$= 12 Hz, C$_6$ - H and C$_7$ - H).

EXAMPLE 6

Cleavage of the silyl groups

1α-hydroxy-3,25-bis triethylsilyloxy cis vitamin D$_3$ (also known as 3,25-bis triethylsilyloxy 1α,3β,25 calcitriol) in THF (103 mg, in 2 ml) is stirred overnight in the presence of tetra n-butylammonium fluoride (5 ml. of a 0.36 M solution in THF). Work-up and prep. TLC afford 64 mg. of 1α,25-dihydroxy cis vitamin D$_3$ (also known as calcitriol), which crystallises in chloroform (53 mg). m.p. (CHCl$_3$ adduct): 103°–106° C. litt: 106°–112° C. $^1$H NMR (acetone d-6):δ0.57 (s, 3H, C$_{18}$ - H). 0.95 (d, J=6 Hz, 3H, C$_{21}$ - H) 1.17 (s, 6H, C$_{26}$ and C$_{27}$ - H). 3.76 to 4.56 (2m, 2H, C$_1$ - H and C$_3$ - H) 4.83 and 5.3 (2m, 2H, C$_{19}$ - H). 6.13 and 6.27 (AB system J$_{AB}$=11 Hz, C$_6$ and C$_7$ - H).

EXAMPLE 7

1α-hydroxy-3-t-butyldimethylsilyloxy vitamin D$_3$ (a) A solution of N-methylmorpholine N-oxide, monohydrate (660 mg) in CH$_2$Cl$_2$ (5 ml) was stirred with anhydrous MgSO$_4$ for 30 min. and filtered through glass wool into a solution of 3-t-butyldimethylsilyloxy trans vitamin D$_3$ 545 mg) in 1,2-dichloroethane (5 ml). The mixture was warmed to reflux and a solution of selenous acid (140 mg), N-methylmorpholine (110 mg; 1 eq) in acetonitrile (5 ml) was quickly added. After 25 min. at reflux, the mixture was diluted with CH$_2$Cl$_2$ and washed with saturated aqueous NaHCO$_3$ solution followed by saturated NaCl aqueous solution. The organic solution was dried over anhydrous Na$_2$SO$_4$ and evaporated to dryness. The residue was chromatographed on silica gel (GB-254 Uniplate 1 mm) to yield the title product (360 mg - 64%).

(b) Tetrabutylammonium hydroxide (0.9 ml of a 1M solution) in MeOH was added to a solution of selenous acid (115 mg) in MeOH. After evaporation of MeOH, the residue was dissolved in acetonitrile (5 ml). The solution was added to a mixture of 3-t-butyldimethylsilyloxy transvitamin D$_3$ (460 mg), N-methylmorpholine N-oxide (550 mg) in CH$_2$Cl$_2$ (5 ml) and 1,2-dichloroethane (5 ml) at reflux. TLC monitoring indicated a very slow conversion to the 1α-hydroxy derivative. After 1 hour at relfux, N-methylmorpholine tosylate (100 mg) was added to the mixture which was refluxed for a further 50 min. After work-up and PLC, 1α-hydroxy 3-t-butyldimethylsilyloxy transvitamin D$_3$ was obtained (260 mg - 55%).

(c) A solution of N-methylmorpholine N-oxide mono-hydrate (180 mg) in CH$_2$ Cl$_2$ (1.5 ml) was dried over MgSO$_4$ for 30 min. and evaporated to dryness. The residue, dissolved in THF (1.5 ml) was added to a solution of 3-t-butyldimethylsilyloxy transvitamin D$_3$ (150 mg) in THF (1.5 ml) and warmed to reflux. A solution of selenous acid (35 mg) and N-methyl morpholine (75 mg) in acetronitrile (1.5 ml) was added quickly. After 1 hour at reflux, aqueous work-up followed by PLC gave unreacted vitamin (47 mg - 31%) and 1α-hydroxy 3-t-butyldimethylsilyloxy transvitamin D$_3$ (82 mg - 53%).

(d) A solution of selenous acid (70 mg), N-methyl morpholine (140 mg) in acetonitrile (3 ml) was quickly added to a solution of 3-t-butyldimethylsilyloxy transvitamin D$_3$ (278 mg), N-methylmorpholine N-oxide, monohydrate (335 mg - 4.4 eq. of water) in THF (6 ml) previously warmed to reflux. After 2 hours at reflux, aqueous work-up and PLC gave unreacted vitamin (60 mg - 21%) and 1α-hydroxy-3-t-butyldimethylsilyloxy transvitamin D$_3$ (94 mg - 33%).

(e) A solution of selenous acid (63 mg), N-methylmorpholine (125 mg) in acetonitrile (2.5 ml) was added to a solution of 3-t-butyldimethylsilyloxy transvitamin D$_3$ (252 mg), N-methylmorpholine N-oxide, monohydrate (320 mg) and water (0.17 ml) in THF (5 ml). After 2 hrs 30 at reflux followed by aqueous work-up and PLC, unreacted vitamin (65 mg - 26%) and 1α-hydroxy 3-t-butyldimethylsilyloxy transvitamin D$_3$ (98 mg - 37%) were obtained.

EXAMPLE 8

1α-Hydroxy-3-t-butyldimethylsilyloxy transvitamin D$_3$
Oxidation with selenium dioxide in methanol N-methylmorpholine N-oxide, monohydrate (285 mg) was stirred with anhydrous MgSO$_4$ in CH$_2$Cl$_2$ (2.5 ml) for 30 min. and then filtered through glass wool into a solution of 3-t-butyldimethylsilyloxy transvitamin D$_3$ (240 mg) in 1,2-dichloroethane (2.5 ml). The mixture was warmed to reflux and a solution of selenium dioxide (50 mg) in methanol (2.5 ml) was quickly added. After 35 min. at reflux the mixture was diluted with CH$_2$Cl$_2$ and worked up. After PLC, 1α-hydroxy-t-butyldimethylsilyloxy transvitamin D$_3$ was obtained (161 mg - 65%).

EXAMPLE 9

1α-Hydroxy-3-t-butyldimethylsilyloxy transvitamin D$_3$

A suspension of selenium dioxide (25 mg) in acetonitrile (1.5 ml) was stirred for 40 min. at room temperature and quickly added to a solution of 3-t-butyldimethylsilyloxy transvitamin D$_3$ (125 mg), N-methylmorpholine N-oxide monohydrate (150 mg) in CH$_2$Cl$_2$ (1.5 ml) and 1,2-dichloroethane (1.5 ml) at reflux. After 25 min at reflux, aqueous work-up and PLC gave 1α-hydroxy-3-t-butyldimethylsilyloxy transvitamin D$_3$ (85 mg 66%).

It should be noted that in Examples 7-9 some of the corresponding 1β-hydroxy isomer was formed but the ratio of 1α-hydroxy to 1β-hydroxy compound was always greater then 20:1.

EXAMPLE 10

(a) 3β-(triethylsilyloxy)-5,6-transvitamin $D_2$

To the 3β-alcohol corresponding to the title compound (4.3 g) in $CH_2Cl_2$ (50 ml) was added imidazole (4 g) followed by triethylsilylchloride (3 ml). After a few minutes, water was added to the organic layer washed with water/brine and dried. The required silyl ether was isolated essentially quantitatively after chromatography as an oil. UV λmax 274nm; $^1$Hnmr δ6.45 and 5.87 (ABq, J=11 Hz, C-6H, 7H), 5.2 (m, W=9 Hz, C-22H, 23H), 4.92 (s, C-19H), 4.63 (s, C-19H), 3.82 (m, W=18 Hz, C-3H).

(b) 1α-hydroxy-3β-(triethylsilyloxy)-5,6-transvitamin $D_2$

N-methylmorpholine N-oxide (NMO) (6.3 g) was stirred with anhydrous $MgSO_4$ in $CH_2Cl_2$ (50 ml) for 30 min. Selenium dioxide (1.3g) was stirred in methanol (50 ml) for 45 min and warmed to reflux. The above $CH_2Cl_2$ mixture was filtered into a solution of the 5,6-transergocalciferol derivative from (a) above (5.5g) in 1,2-dichloroethane (50 ml). This mixture was warmed to reflux and then the hot methanol mixture added, and refluxing of the whole continued for a further 35 min. The heat source was removed and the mixture diluted with $CH_2Cl_2$. Aqueous work-up followed by chromatography through silica gel (40 g) gave 2.66 g (47%) of the title compound as an oily product. UV λmax 274nm; $^1$Hnmr δ6.57 and 5.90 (ABq, J=11 Hz, C-6H, 7H), 5.25 (m, W=9Hz, C-22, 23H), 5.08 (s, C-19H), 4.98 (s, C-19H), 4.65-3.92 (m, C-1H, 3H).

(c) 1α-hydroxy-5,6-transvitamin $D_2$

The silylether from (b) above (460 mg) in THF (10 ml) was stirred for 30 min with tetrabutylammonium fluoride (460 mg). The mixture was diluted with $CH_2Cl_2$ and after aqueous work-up, the title diol was purified by plc to give 305 mg (84%). Crystalline from ether/hexane. m.p. 103°-105° C.; $[\alpha]_D = +172°$ (c=0.58); UV λmax 272nm (22600); $^1$Hnmr δ6.38 and 5.82 (ABq. J=11 Hz, C-6H, 7H), 5.18 (m, W=9 Hz, C-22H, 23H), 4.9 (m, W=9 Hz, C-19$H_2$), 4.53-3.77 (m, C-1H, 3H), 0.57 (s, C-18$H_3$); IR νmax 3500 (s), 2950 (s), 2900 (sh), 1640 (w), 1460 (m), 1375 (m), 1050 (s), 1030 (s), cm$^{-1}$; mass spec. molecular ion m/e=412; (analysis found: % C, 79.57; H, 10.71; $C_{28}H_{44}O_2$ requires: % C, 81.50; H, 10.79; $C_{28}H_{44}O_2 \cdot \frac{1}{2}H_2O$ requires: % C, 79.76; H, 10.76).

(d) 1α-hydroxy-3β-triethylsilyloxy-cis vitamin $D_2$

The 5,6-trans compound from (b) above in benzene (30 ml) containing phenazine (120 mg) and triethylamine (few drops) was photoisomerised as above for 30 min to give 400 mg (66%) of the title 5,6-cis vitamin, UV λmax 263 nm; $^1$Hnmr δ6.38 and 6.08 (ABq, J=11 Hz, C-6H, 7H), 5.23 (m, W=10 Hz, C-19H, 22H, 23H), 5.0 (s, C-19H), 4.6-3.92 (m, C-1H, 3H).

(e) 1α-hydroxy-cis vitamin $D_2$

The silyl ether derivative from (d) above (200 mg) was stirred at room temperature in THF (10 ml) with N-$Bu_4$NF (1 M soln. in THF, 2 ml) for about 30 min. Dilution with $CH_2Cl_2$ and aqueous work-up followed by purification by plc gave 129 mg (82%). Crystalline from ether/hexane gave the title compound. m.p. 141°-143° C. (lit. 138°-140° C.) $[\alpha]_D = +34°$ (c=0.645); UV λmax 264 nm (19100); $^1$Hnmr δ6.35 and 6.05 (ABq, J=11 Hz, C-6H, 7H), 5.16 (m, W=14 Hz, C-19H, 22H, 23H). 4.98 (s, C-19H), 4.6-3.85 (m, C-1H, 3H), 0.55 (s, C-18$H_3$); IR νmax 3500 (s), 2950 (s), 2900 (sh), 1640 (w), 1460 (m), 1060 (s), cm$^{-1}$; mass spec. molecular ion m/e=412; (analysis: $C_{28}H_{44}O_2$ requires: % C, 81.50; H, 10.75; 0, 7.76; found: % C, 81.39; H, 10.60).

EXAMPLE 11

9,10-seco-1α,3β-dihydroxy-20(S)-(p-toluenesulphonyloxymethyl)-23,24,25,26,27 pentakis nor cholesta-5(Z), 7(E), 10(19)-triene

(i) 9,10-seco-1α-hydroxy-3β-(triethylsilyloxy)-20(S)-(p-toluenesulphonyloxymethyl)-23,24,25,26,27 pentakis nor cholesta-5(E), 7(E), 10(19)-triene Selenium dioxide (56 mg) was stirred in acetonitrile (3.5 ml) for 45 min. N-methylmorpholino N-oxide monohydrate NMO (280 mg) was stirred in $CH_2Cl_2$ (3.5 ml) in the presence of anhydrous $MgSO_4$ for 30 min. The NMO solution was filtered into a solution of the 1-desoxy compound (prepared as described in Preparation 4) (308 mg) in 1,2-dichloroethane (3.5 ml) and the mixture warmed to reflux. To this was added the $SeO_2/CH_3CN$ mixture, and refluxing continued for a further 5.5 min. The reaction mixture was cooled in an ice bath, diluted with $CH_2Cl_2$ and worked up as described previously to give 180 mg (57%) of the title 1-hydroxy compound. $^1$Hnmr δ7.73 (d, J=8 Hz, 2H, aryl), 7.28 (d, J=8 Hz, 2H, aryl), 6.43 and 5.81 (ABq, J=11 Hz, C-6H, 7H), 5.03 (s, C-19H), 4.93 (s, C-19H), 4.63-3.6 (m, C-1H, 3H, 22$H_2$), 2.48 (s, aryl-$CH_3$).

(ii) 9,10-seco-1α-hydroxy-3β-(triethylsilyloxy)-20(S)-(p-toluenesulphonyloxymethyl)-23,24,25,26,27 pentakis nor cholesta-5(Z), 7(E), 10(19)-triene The corresponding 5(E) compound from (i) above (225 mg) in benzene (35 ml) containing triethylamine (3 drops) was irradiated as described above with anthracene (45 mg) as triplet sensitiser for 30 min to give, after plc, 185 mg (82%) of the title compound. UV max 263 nm and 216 nm; $^1$Hnmr δ7.73 (d, J=8 Hz, 2H, aryl), 7.3 (d, J=8Hz, 2H, aryl), 6.28 and 5.98 (ABq, J=11 Hz, C-6H, 7H), 5.28 (s, C-19H), 4.92 (s, C-19H), 4.55-3.58 (m, C-1H, 3H, 22H2), 2.45 (s, aryl-$CH_3$).

(iii) 9,10-seco-1α-3β-dihydroxy-20(S)-(p-toluenesulphonyloxymethyl)-23,24,25,26,27 pentakis nor cholesta-5(Z), 7(E), 10(19)-triene The silyl ether from Example 43 (185 mg) in THF (5 ml) containing n-$Bu_4$NF (1 M soln in THF, 0.32 ml) was stirred for 15 min at room temperature. Dilution with $CH_2Cl_2$ aqueous work-up and purification by plc gave the title diol (110 mg, 73%). UV max 263 nm ( 17427) and 216 nm (18672): $^1$Hnmr δ7.68 (d, J=8 Hz, 2H, aryl) 7.23 (s J=8 Hz, 2H, aryl), 6.28 and 5.97 (ABq, J=11 Hz, C-6H, 7H), 5.27 (s,C-19H), 4.93 (s, C-19H), 4.57-3.6 (m, C-1H, 3H, 22$H_2$), 2.45 (s, aryl-$CH_3$), 1.05 (d, J=6 Hz, C-21$H_3$), 0.52 (s, C-18$H_3$).

We claim:

1. A process for the 1α-hydroxylation of vitamin D compounds by $SE^{IV}$ oxidation which comprises the oxidation of a 1-unsubstituted 5,6-trans vitamin D compound of formula I:

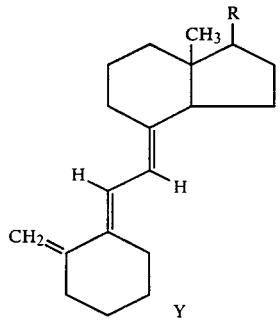

(I)

wherein Y represents a hydrogen atom, a hydroxyl group, an alkanoyloxy group having 1 to 6 carbon atoms, an aroyloxy group having 7 to 15 carbon atoms, a lower alkoxy group having 1 to 6 carbon atoms which may be interrupted by an oxygen atom, a tetrahydropyranyloxy group or a trihydrocarbylsilyloxy group and R represents a group of the formula:-

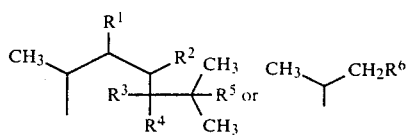

wherein $R^1$, $R^2$, $R^3$, and $R^5$ which may be the same or different, each represents a hydrogen or halogen atom, a hydroxy group, an alkanoyloxy group having 1 to 6 carbon atoms, an aroyloxy group having 7 to 15 carbon atoms, a lower alkoxy group having 1 to 6 carbon atoms which may be interrupted by an oxygen atom, a tetrahydropyranyloxy group or a trihydrocarbylsilyloxy group, or $R^1$ and $R^2$ may together form a carbon-carbon bond or an epoxy group; $R^4$ represents a hydrogen or halogen atom or a methyl or ethyl group, or $R^3$ and $R^4$ together represent a keto or protected keto group; and $R^6$ represents a hydroxy or hydrocarbylsulphonyloxy group in the presence of a selenous acid at a pH in the range 3-9.

2. A process as claimed in claim 1 wherein the selenous acid is generated in situ by the use of selenium dioxide in the presence of water.

3. A process as claimed in claim 1 wherein the water is present in the reaction mixture in the form of a hydrated reactant.

4. A process as claimed in claim 4 wherein the oxidation is effected by the use of selenium dioxide and water, the ratio of selenium dioxide to water being in the range 0.1 to 50 by weight.

5. A process as claimed in claim 1 wherein the oxidation is effected in the presence of a buffer system.

6. A process as claimed in claim 1 wherein the oxidation is effected by the use of a salt of a strong base with selenous acid.

7. A process as claimed in claim 1 wherein a compound of formula I is used in which R represents the group:

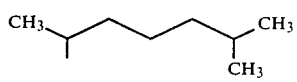

8. A process as claimed in claim 1 wherein the oxidation is effected in the presence of a co-oxidant capable of oxidising $Se^{II}$ compounds to $Se^{IV}$ compounds selected from the group consisting of peracids, alkyl hydroperoxides in which the alkyl moiety may be substituted by aryl, and nonaromatic tertiary amine oxides.

9. A process as claimed in claim 1 for the 1α-hydroxylation of vitamin D compounds by $Se^{IV}$ oxidation which comprises the oxidation of a 1-unsubstituted-3-trihydrocarbylsilyloxy-5,6-trans vitamin D compound at a pH in the range 3-9 in the presence of a selenous acid and co-oxidant capable of oxidising $Se^{II}$ compounds to $Se^{IV}$ compounds selected from the group consisting of metal salts of peracids, alkyl hydroperoxides in which the alkyl moiety may be substituted by aryl, and nonaromatic tertiary amine oxides.

10. A process as claimed in claim 1 wherein the 1α-hydroxy-5,6-trans vitamin D thus formed is isomerized to a 1α-hydroxy-5,6-cis vitamin D, any protecting groups present optionally being removed.

* * * * *